United States Patent [19]

DiGiulio et al.

[11] 4,080,440

[45] Mar. 21, 1978

[54] METHOD FOR REMINERALIZING TOOTH ENAMEL

[75] Inventors: David N. DiGiulio, Springfield Township, Hamilton County; Robert J. Grabenstetter, Colerain Township, Hamilton County, both of Ohio

[73] Assignee: The Procter & Gamble Company, Cincinnati, Ohio

[21] Appl. No.: 670,473

[22] Filed: Mar. 25, 1976

Related U.S. Application Data

[63] Continuation-in-part of Ser. No. 532,443, Dec. 13, 1974, abandoned, which is a continuation-in-part of Ser. No. 513,211, Oct. 10, 1974, abandoned, which is a continuation-in-part of Ser. No. 415,484, Nov. 13, 1973, abandoned.

[51] Int. Cl.$^2$ ............... A61K 7/16; A61K 7/18; A61K 33/42; A01N 11/00
[52] U.S. Cl. ............................ 424/49; 424/52; 424/57; 424/128; 424/154
[58] Field of Search ................ 424/49, 154, 52, 57

[56] References Cited

U.S. PATENT DOCUMENTS

| | | | |
|---|---|---|---|
| 1,222,144 | 4/1917 | Ruthrauff | 424/49 |
| 2,154,168 | 4/1939 | Klein et al. | 424/49 |
| 3,175,951 | 3/1965 | Tucker et al. | 424/52 |
| 3,225,914 | 12/1965 | Klein | 206/223 |
| 3,679,360 | 1/1972 | Rubin et al. | 424/128 |

FOREIGN PATENT DOCUMENTS

| | | | |
|---|---|---|---|
| 1,434,455 | 4/1966 | France | 424/49 |
| 1,090,340 | 11/1967 | United Kingdom. | |

OTHER PUBLICATIONS

Accepted Dental Therapeutics, 35th Edition, p. 255, (1/73).
Feagin et al., Arch. Oral Biol. 16, pp,. 535–548.
Souder et al., J. Am. Dental Assoc., 31, 23, pp. 1579–1586, (1944).
Public Health Reports, 63, 38, pp. 1215–1221, (9/17/48).
Grabenstetter et al., Chemical Abstracts 81:29518h, (1974).
Levine (1), Arch Oral Biol., vol. 17, pp. 1005–1008, 1972.
Levine (2), Arch. Oral Biol. pp. 1351–1356, (1973).
Levine (3), Brit. Dent. J., pp. 132–134, (1974).

*Primary Examiner*—Albert T. Meyers
*Assistant Examiner*—D. W. Robinson
*Attorney, Agent, or Firm*—George W. Allen; Douglas C. Mohl; Eric S. Spector

[57] ABSTRACT

Demineralized tooth enamel is remineralized by first forming a metastable mixture by mixing a solution containing a soluble calcium salt with a solution containing a soluble phosphate salt, the mixture having a pH of from about 2.5 to about 4 and a ratio of calcium ions to phosphate ions of from 0.01 to 100; and second, applying the metastable mixture to the tooth surface. Preferably, the second solution contains a soluble fluoride salt and the metastable mixture has a pH of about 2.7.

12 Claims, No Drawings

METHOD FOR REMINERALIZING TOOTH ENAMEL

CROSS-REFERENCE TO RELATED APPLICATIONS

This application is a continuation-in-part of application Ser. No. 532,443, filed Dec. 13, 1974, now abandoned, which is a continuation-in-part of application Ser. No. 513,211, filed Oct. 10, 1974, now abandoned, which, in turn, is a continuation-in-part of application Ser. No. 415,484, filed Nov. 13, 1973, now abandoned.

BACKGROUND OF THE INVENTION

1. Field of the Invention

This invention relates to a process for remineralizing dental enamel in which solutions containing calcium and phosphate ions are mixed to form a metastable solution which is applied to dental enamel, resulting in remineralization of the dental enamel and efficacy against caries.

2. The Prior Art

It is well known in the dental art that dental caries begin as a subsurface demineralization ("white spots") of the dental enamel and that remineralization or recalcification may be of importance in retarding or arresting dental caries. However, heretofore no method was known by which a member of the general public could conveniently effect remineralization of subsurface dental enamel. Ruthrauff; U.S. Pat. No. 1,222,144, issued Apr. 10, 1917 teaches acidic dentifrice compositions for remineralizing tooth enamel comprising a soluble calcium salt, and an agent for more effectively causing the solution to permeate and completely fill up the minute spaces in the tooth surface. Klein et al; U.S. Pat. No. 2,154,168; issued Apr. 11, 1939 discloses dentifrices containing calcium and phosphate ions and having a pH of from about 5 to about 10. Rubin et al; U.S. Pat. No. 3,679,360; issued July 25, 1972, discloses a method, the purpose of which is to deposit calcium phosphate from a gel medium onto the tooth surface. The surface on which calcium phosphate growth is desired is prepared (as by roughening) and the tooth and coatings are covered by a suitable cap for several days while the remineralization takes place. Warner Lambert's British Pat. No. 1,090,340 discloses the use of slightly alkaline supersaturated calcium phosphate solutions to effect some degree of emanel remineralization.

In spite of the above described prior art remineralization attempts, there is a continuing need for compositions and methods by which remineralization can be conveniently and effectively accomplished. Abandoned U.S. application Ser. No. 297,517, filed Oct. 13, 1972, Robert John Grabenstetter and John Augustus Gray, III, entitled "PROCESSES AND COMPOSITIONS FOR REMINERALIZATION OF DENTAL ENAMEL" and its subsequently filed related applications (Ser. No. 438,973, filed Feb. 4, 1974 and Ser. No. 561,830, filed Apr. 2, 1975, now both abandoned) teaches a method of remineralizing subsurface dental enamel in which two compositions containing, respectively, a cation and an anion, such as calcium ion and phosphate ion, are sequentially applied to the dental enamel. This method, while successful, requires sequential application of the respective solutions. The present invention, on the other hand, provides a method by which subsurface dental enamel can be mineralized by the application of one solution to the tooth surface.

SUMMARY OF THE INVENTION

In accordance with the present invention, demineralized tooth enamel is remineralized by:

(A) first, mixing a first solution containing a soluble calcium salt yielding from about 0.005% to about 5% (preferably from about 0.25% to about 5%) of calcium ions with a second solution containing a soluble phosphate salt yielding from about 0.005% to about 5% (preferably from about 0.25% to about 5%) of phosphate ions, said mixture having a pH of from about 2.5 to about 4.0 and a molar ratio of calcium ions to phosphate ions of from about 0.01 to about 100;

(B) second, within 5 minutes after forming said mixture, applying a therapeutic amount of said mixture to a tooth surface for a period of time of from about 10 seconds to about 3 minutes.

In a preferred embodiment of the present invention, the second solution additionally contains a soluble salt of an anion capable of forming an insoluble precipitate with calcium, magnesium or heavy metal cations, said soluble salt yielding from about 0.005% to about 5%, preferably from about 0.005% to about 0.1% of said anions. Preferred anions are fluoride, fluorophosphate, fatty acid radicals having from 8 to 18 carbon atoms and carbonate. Fluoride is most preferred. Most preferably, the mixture has a pH of about 2.7. If the remineralization contemplated by this invention is carried out in accordance with this preferred embodiment, an antisolubility effect results, i.e., the remineralized enamel is more resistant to demineralization than was the original enamel.

DESCRIPTION OF THE INVENTION

The present invention lies in the discovery that demineralized dental enamel may be remineralized by applying to the teeth a metastable solution of calcium and phosphate ions which will diffuse through the tooth surface to the demineralized subsurface and precipitate, resulting in remineralization or recalcification of subsurface dental enamel. The metastable solution is made by mixing a first solution, also referred to herein as the "cationic" solution, containing a water-soluble calcium salt yielding from about 0.005% to about 5% by weight of the first solution of calcium cations, (preferably from about 0.25% to about 5%), with a second solution, also referred to herein as the "anionic" solution, containing a water-soluble phosphate salt yielding from about 0.005% to about 5% phosphate anions by weight of the second solution (preferably from about 0.25% to about 5%), said mixture having a pH of from about 2.5 to about 4, and a molar ratio of calcium cations to phosphate anions of from about 0.01 to 100 (i.e., 0.01:1 to 100:1). Unless specified otherwise, all percentages referred to herein are percentages by weight.

The water-soluble calcium salts suitable for use in the present invention can be any water-soluble calcium salt which is safe for use in the oral cavity. The solubility should preferably be at least about 0.07% in water at 100° C. Examples of suitable calcium salts are calcium chloride, calcium acetate, calcium formate, calcium lactate and calcium nitrate. Likewise, the phosphate salts suitable for use can be any of the water-soluble phosphate salts which are suitable for use in the oral cavity and having a solubility of at least 0.07% in water at 100° C. Phosphoric acid is also suitable for use, and for purposes of brevity, it will be understood that when the term "phosphate salts" is used herein, it is intended to also include phosphoric acid. Examples of suitable water-soluble phosphate salts are disodium hydrogen phosphate, sodium dihydrogen phosphate, potassium dihydrogen phosphate and trisodium phosphate.

It is preferred to remineralize the tooth structure with a precipitate which has antisolubility characteristics, i.e., with a precipitate which is more resistant to demineralization than was the original enamel. Thus, it is preferred that the first solution have a pH of less than about 5 and contain a soluble salt of magnesium or a heavy metal yielding from about 0.005% to about 5% of the first solution, preferably from about 0.005% to about 0.1%, of magnesium or heavy metal cations in addition to the calcium salt, that the second solution additionally contain a soluble salt of an anion capable of forming an insoluble precipitate with calcium, magnesium or heavy metal cation, said salt yielding from about 0.005% to about 5% by weight of the second solution, preferably from about 0.005% to about 0.1% of said anions, and that the metastable mixture have a pH of about 2.7.

While applicants do not wish the scope of the present invention to be limited by theory, it is believed that the calcium and phosphate ions diffuse through the tooth surface to the demineralized subsurface while the mixture is in the metastable state and precipitate in the demineralized subsurface where they remineralize the tooth structure. This is accomplished by employing a metastable solution in which the calcium and phosphate ions remain soluble for a period of time sufficient to permit their diffusion into the demineralized subsurface of the dental enamel. More specifically, this is accomplished by combining the particular ions just prior to their application to the tooth in a solution having a pH of from about 2.5 to about 4, at which pH the calcium and phosphate ions remain soluble for the period of time required. The calcium and phosphate ions are stored separately to avoid the premature precipitation of calcium phosphate.

Chemically equivalent concentrations of the first and second solutions are not necessary so long as the molar ratio of calcium and phosphate ions in the mixture is from 0.01 to 100. It is preferred that the ratio is from about 0.2 to about 5 and it is most preferred that the ratio is about 1.67, the ratio of calcium to phosphate in natural teeth enamel (hydroxyapatite).

While completely aqueous solutions are preferred in the present invention, non-aqueous solvents may be employed in combination with water. For example, suitable nonaqueous solvents include ethyl alcohol, glycerine and propylene glycol. Solvent systems suitable for use in the present invention are those which are capable of dissolving the salts employed in the invention and which are safe for use in the mouth.

In considering the period of time of exposure of the metastable solution to the tooth, it is necessary that the length of time be great enough to allow diffusion of the ions into the demineralized subsurface. At least about ten seconds are required for this diffusion. The solution is preferably applied to the teeth for from about 10 seconds to about 3 minutes. The pH of the solution will rise due to natural factors after its introduction into the oral cavity. Calcium phosphate precipitates during this rise in pH, but after calcium ions and phosphate ions have diffused into the demineralized tooth enamel. It is believed that the ability of the metasable solution to provide ions for remineralization is greatest upon its first introduction into the oral cavity, thereafter decreasing.

The time period between the mixing of the first and second solutions and the application of the mixture to the teeth should not exceed 5 minutes, and preferably is less than 1 minute. The essence of the present invention lies in the creation of a metastable solution which will precipitate calcium phosphate and, in the most preferred embodiment, also indium phosphate and calcium fluoride, in the subsurface enamel of the teeth. Before such precipitation occurs, the solution is applied to the teeth. The solution must have a pH of about 4 or below to achieve this result. At a pH above about 4, precipitation occurs too rapidly. A pH below 2.5 is generally undesirable from a safety standpoint and adds nothing to the invention. By maintaining the pH of the metastable solution within the 2.5-4 range before introduction into the mouth, it is not necessary to employ such materials as sodium chloride to enhance the stability of the metastable solutions formed. Accordingly, the metastable solutions herein can be substantially free of sodium chloride.

Although one would expect an acidic solution to demineralize the teeth, the use of the metastable solution of the present invention, which is saturated or supersaturated with respect to calcium phosphate, results in remineralization instead of demineralization.

The pH of the solutions of the present invention may be adjusted to the pH desired by methods well known in the art. The pH may be lowered by the addition of any acid which is safe for use in the oral cavity and which yields the desired pH at the amount employed. Examples of suitable acids are hydrofluoric acid, phosphoric acid, hydrochloric acid, citric acid and malic acid. Should the pH be lower than desired, an appropriate amount of sodium hydroxide may be added to raise it. The appropriate acid can be added to the mixture of the first and second solutions immediately upon mixing or, preferably, the acid can be incorporated into one or both of the solutions before mixing in amount such that the two solutions have the required pH after mixing.

In order to effect remineralization of the dental enamel, a therapeutic amount of a solution of calcium and phosphate ions must be employed in the mouth. The amount of solution placed in the mouth must contain at least 0.001 g. of calcium phosphate, and preferably contains more than 0.1 g. of calcium phosphate to be effective.

If the demineralized subsurface dental enamel is remineralized with a precipitate which is less soluble than the original enamel, the remineralized subsurface is more resistant to demineralization than was the original enamel. If the remineralization contemplated by this invention is carried out in accordance with the preferred embodiments, the remineralized enamel is more resistant to demineralization than was the original enamel because magnesium or heavy metal cations and/or certain anions such as fluoride ions, which are capable of forming insoluble precipitates with calcium, magnesium or heavy metal cations (hereinafter also referred to as secondary anions) are incorporated into the remineralized tooth structure. If both types of ions are so incorporated, the remineralized enamel is even more resistant to demineralization than if only one type of ion is incorporated. The concentration of magnesium or heavy metal cation and secondary anion in the respective solutions may be from about 0.005% to about 5%, and is preferably from about 0.005% to about .1%.

Examples of non-calcium heavy metal cations suitable for incorporation into the first, or cationic solution, herein include soluble salts of manganese, tin, zinc, indium, zirconium, iron, titanium, vanadium, rare earth metals such as lanthanum and cerium, and aluminum. Tin, indium, magnesium, and rare earth metals and aluminum are preferred; indium is most preferred. Suitable soluble salts of these cations include the halide (e.g., chloride), nitrate, sulfate, acetate and gluconate salts of the desired cation. For example, suitable soluble indium salts include indium chloride, indium sulfate, and indium nitrate.

Examples of non-phosphate anions which will react with cations to give desirable insoluble precipitates, and are therefore suitable for incorporation into the second, or anionic solutions, herein include fatty acid groups having from 8 to 18 carbon atoms, and alkyl sulfonates having from 6 to 18 carbon atoms. Other such anions include fluoride, fluorophosphate, silicofluoride, molybdate, sulfate, tungstate, tartrate, sorbate, carbonates, and iodates. Fluoride, fluorophosphate, silicofluoride, sorbate, sulfate, tartrate, carbonate are the preferred non-phosphate anions. Fatty acids having from 8 to 18 carbon atoms, e.g., laurate and stearate, are also preferred non-phosphate anions. Suitable salts of these secondary anions include the water-soluble sodium, potassium, ammonium and substituted ammonium salts. The most preferred secondary anion is fluoride ion. Examples of soluble fluoride salts which are suitable for use in the second solution of the present invention include sodium fluoride, zinc fluoride, betaine fluoride, alanine stannous fluoride, and hexylamine fluoride. Hydrofluoric acid can also be used.

Like the calcium and phosphate salts, the non-calcium and non-phosphate salts employed respectively in the cationic and anionic solutions are water-soluble. Solubility of such salts is preferably at least about 0.07% in water at 100° C.

It will be recognized by those skilled in the art that many different precipitates can be formed by a solution made in accordance with the present invention. It is preferred that the precipitate be white in color. Some of these precipitates may be formed by first forming an original precipitate which then further reacts to form the indicated precipitate. For example, a hydroxide may form first and then react further to form the corresponding oxide. It is most preferred that the ingredients of the present invention are selected so that most precipitates are calcium phosphate compounds with small amounts of indium and fluoride incorporated therein. This results in a remineralized tooth structure which is similar to the natural tooth structure with small amounts of indium and fluoride incorporated therein, resulting in increased resistance to solibility. Thus, the remineralized tooth structure will be more resistant to dental caries than was the original structure.

By employing suitable ions in the present composition, the following insoluble precipitates in addition to calcium phosphate may be formed: $CaF_2$, $ZnNH_4PO_4$, $InPO_4$, rare earth phosphates such as lanthanum, cerium, and samarium phosphate, rare earth fluorides such as lanthanum, cerium, praseodymium, neodynium, and samarium fluorides, magnesium alkyl sulfonate wherein the alkyl group has from 10 to 22 carbon atoms, magnesium stearate, calcium stearate, zinc stearate, and aluminum phosphate.

Other precipitates contemplated by this invention are: Aluminum oxide; aluminum hydroxide; indium hydroxide; indium phosphate; lanthanum tartrate; lanthanum sorbate; lanthanum oxalate; lanthanum oxide; lanthanum tungstate; lanthanum phosphate; magnesium alkyl sulfonates such as magnesium n-decyl sulfonate, magnesium lauryl sulfonate, magnesium myristyl sulfonate, magnesium cetyl sulfonate, and magnesium n-octadecyl sulfonate; magnesium oleate; magnesium myristate; magnesium palmitate; magnesium stearate; magnesium laurate; magnesium carbonate; magnesium floride; magnesium phosphates; magnesium hydroxide; magnesium ammonium phosphate; manganese carbonate; manganese hydroxide; manganese ammonium phosphate; nickel hydroxide; laurate; myristate; palmitate; stearate; stannous oxalate; zinc tartrate; zinc carbonate; zinc oxalate; zinc hydroxide; zinc phosphate (usually complex mixtures); zinc ammonium phosphate; zirconium hydroxide; zirconium phosphate; calcium carbonate; calcium molybdate; calcium silicate; calcium tungstate; calcium lauryl sulfonate; calcium myristyl sulfonate; calcium n-hexadecyl sulfonate; calcium n-octadecyl sulfonate; calcium oleate; calcium stearate; calcium tartrate; calcium aluminates; calcium hydroxide; calcium ammonium phosphate; tricalcium phosphate; dicalcium phosphate; calcium monofluorophosphate; $MgHPO_4$; $Mg_3(PO_4)_2$; $MgNH_4PO_4$; aluminum phosphates; aluminum orthophosphate; calcium phosphates, zinc phosphates; strontium phosphate; indium phosphate; tin phosphate; ceric phosphate; $MoO_3$; $SiO_2$; $SiO_2xH_2O$; $Sn(OH)_2$; $SnO \cdot xH_2O$; $Ti(OH)_4$; $TiO_2$; $V_2O_5$; and $WO_3$. These precipitates are formed by using the appropriate cations in the first solution and the appropriate anions in the second solution as described above.

For commercial exploitation of the present invention, it is contemplated that "kits" will be made which will enable the consumer to make a metastable solution and apply it to the teeth. Suitable kits can comprise two separately packaged solutions of the respective cations and anions, but more preferably, the kits are in the form of a two-part toothpaste or mouthwash composition. The two parts, a cationic portion and an anionic portion, should be packaged to facilitate mixing the two parts and then applying the mixture to the teeth. The term "cationic part" refers to the solution containing from 0.005% to 5% calcium cations, and the term "anionic part" refers to the solution containing from 0.005% to 5% phosphate anions. The solutions in the kit are compounds with respect to acidity and ionic concentration such that mixing of the solutions in proper proportions for use in the process of the present invention will give a pH of from about 2.5 to about 4.0 and a calcium to phosphate molar ratio of from about 0.01 to 100.

The metastable remineralizing solutions herein can be provided in the form of a mouthwash product. Both the cationic and anionic parts of mouthwashes can be made in accordance with the following. Mouthwashes generally comprise an aqueous solution of ethyl alcohol and flavoring materials. The alcohol provides an antibacterial effect and also solubilizes the flavoring materials. Optionally, mouthwashes also contain additional antibacterial agents such as cetyl pyridinium chloride and domiphen bromide, and humectants such as glycerine and sorbitol which give a moist feeling to the mouth.

Typically, mouthwashes contain 3% – 60%, preferably 5% – 30%, ethyl alcohol; 30% – 90% water; 5% – 20% glycerine or other humectant; 0.01% – 0.1% of an antibacterial agent; 0.01% – 0.5% of a sweetening agent, 0.01% – 2.0% of a flavoring agent, and from 0.1% – 1% of an emulsifier-surfactant such as polyoxethylene (20) sorbitan monoisostearate. Examples of suitable flavoring agents include heliotropyl nitrile, wintergreen oil (methyl salicylate), oil of peppermint, oil of cassia, oil of anise, oil of cinnamon, and mixtures thereof. Suitable sweetening agents include saccharin, glycerine, sorbitol, levulose, and 6-(trifluoromethyl)-tryptophane and aspartyl phenylalanine methyl ester.

The present invention can also be embodied in a toothpaste composition and packaged in a codispensing toothpaste tube such as that disclosed in U.S. Pat. No. 3,290,422, Dec. 6, 1966, to Kenneth George Michel, or the abandoned U.S. Patent application of Charles R. Hood and Stephen F. Evans, Ser. No. 415,467, filed Nov. 13, 1973 and entitled "COLLAPSIBLE, LONGITUDINALLY PARTITIONED TUBULAR DISPENSING CONTAINER", now abandoned.

Suitable toothpastes can be made by employing in both the anionic and cationic portions of the toothpaste, from about 0.5% to about 50%, preferably from 5% to 25%, of an abrasive, from about 0.2% to about 5% of a sudsing agent, from about 0.1% to about 5% of a binding agent, from 0% to about 50% of a humectant, and balance, water and minors. The pH of the toothpaste containing the active cationic ingredients has a pH of less than about 5. The mixture of the two portions which is placed in the mouth must have a pH of from about 2.5 to about 4. The pH's of the cationic portion and the anionic portion can be adjusted so long as the above parameters are not exceeded. Should the anionic portion of the toothpaste contain fluoride ions and have a pH of less than 5, the active fluoride might etch the teeth should it be placed in the mouth alone.

Suitable abrasives include silica xerogels such as those disclosed in U.S. Pat. No. 3,538,230, Nov. 3, 1970, to Padar et al., which is incorporated herein by reference. Other conventional toothpaste abrasives can be used in the compositions of this invention, and include beta-phase calcium pyrophosphate, zirconium silicate, the thermosetting polymerized resins described by Cooley et al. in U.S. Pat. No. 3,070,510, Dec. 25, 1962, which is incorporated herein by reference. Silica aerogels and the insoluble metaphosphates such as insoluble sodium metaphosphate can be used. Mixtures of abrasives can be also be used. Silica xerogel abrasives are preferred.

Suitable sudsing agents are those which are reasonably stable and form suds throughout an acidic pH range. Preferably, non-soap anionic or nonionic organic synthetic detergents. Examples of such agents are water-soluble salts of alkyl sulfate having from 10 to 18 carbon atoms in the alkyl radical, such as sodium lauryl sulfate, water-soluble salts of sulfonated monoglycerides of fatty acids having from 10 to 18 carbon atoms, such as sodium monoglyceride sulfonate, salts of $C_{10}$–$C_{18}$ fatty acid amides of taurine, such as sodium N-methyl-N-palmitoyl tauride, sodium N-coconut-acid-N-methyl taurate, salts of $C_{10}$–$C_{18}$ fatty acid esters of isethionic acid, and substantially saturated aliphatic acyl amides of saturated monoaminocarboxylic acids having 2 to 6 carbon atoms, and in which the acyl radical contains 12 to 16 carbon atoms, such as sodium-N-lauryl sarcoside. Mixtures of two or more sudsing agents can be used.

A binding material is added to thicken and provide a desirable consistency for the present compositions. Suitable thickening agents are water-soluble salts of cellulose ethers, such as sodium carboxymethyl cellulose, hydroxypropyl cellulose, and hydroxyethyl cellulose. Natural gums such as gum karaya, gum arabic, and gum tragacanth, can also be used. Colloidal magnesium aluminum silicate, silica aerogels, silica xerogels, fumed silica, or other finely divided silica can be used as part of the thickening agent for further improved texture. A preferred thickening agent is xanthan gum, available from the Kelco Company.

It is also desirable to include some humectant material in a toothpaste to keep it from hardening. Suitable humectants include glycerine, sorbitol, propylene glycol, and other edible polyhydric alchols.

Toothpoaste compositions may also contain flavoring agents such as oil of wintergreen, oil of peppermint, oil of spearmint, oil of sassafras, and oil of clove. Toothpaste compositions may also contain sweetening agents such as saccharin, dextrose, levulose, and sodium cyclamate. A toothpaste and mouthwash illustrating the present invention are set forth in the following examples, which are intended to illustrate, but not to act as a limitation, upon the present invention.

EXAMPLE 1

A suitable two-part toothpaste for use in accordance with the present invention was made of the following ingredients and stored with the anionic and cationic portions separated:

| Ingredient | Anionic Part % by Weight | Cationic Part 5 by Weight |
| --- | --- | --- |
| Disodium phosphate | 0.88 | — |
| Sodium fluoride | 0.20 | — |
| Calcium chloride | — | 2.50 |
| Indium trichloride | — | 0.17 |
| Silica xerogel abrasive (Syloid 620 from the Grace Davison Chem. Co.) | 9.00 | 9.00 |
| Silica zerogel abrasive (Syloid 63 from the Grace Davison Chem. Co.) | 9.00 | 9.00 |
| Polyoxyethylene (200 sorbitan monoisostearate. | 1.00 | 1.00 |
| Igepon TC-42 (a 25% soln. of sodium N-coconut-acid-N-methyl taurate in water from GAF Corp. Chem. Div.) | 7.00 | 7.00 |
| Keltrol xanthan gum (a polysaccharide of high molecular weight from the Kelco Co.) | 1.30 | 1.30 |
| Glycerine | 13.00 | 13.00 |
| Sorbitol (70% soln. in water) | 25.00 | 25.00 |
| Phosphoric acid (85.6% soln. in water) | 0.83 | — |
| Hydrofluoric acid (48% soln. in water) | — | 0.15 |
| Sodium hydroxide (10% soln. in water) | — | 0.45 |
| Coloring agent | 0.03 | — |
| Titanium dioxide | — | 0.50 |
| Flavor | 1.00 | 1.00 |
| Sweetening agent (saccharin) | 0.33 | 0.33 |

| Ingredient | Anionic Part % by Weight | Cationic Part 5 by Weight |
|---|---|---|
| Water | balance | balance |

The anionic paste had a pH of about 5.2. The cationic phase had a pH of about 3.0. One gram portions of each of the above pastes were simultaneously placed in the mouth whereupon the teeth were brushed in the usual manner three times per day for four weeks. The pH of the mixture was about 3.3. Observation indicated that remineralization of demineralized enamel had occurred. The remineralized enamel was more resistant to demineralization that was the original enamel.

EXAMPLE 11

A suitable two-part mouthwash for use in accordance with the present invention was made of the following ingredients and stored with the anionic and cationic parts separated:

| Ingredient | Anionic Part % by Weight | Cationic Part % by Weight |
|---|---|---|
| Disodium phosphate | 1.69 | — |
| Sodium fluoride | 0.07 | — |
| Calcium chloride | — | 2.22 |
| Indium trichloride | — | 0.06 |
| Glycerine | 10.00 | 10.00 |
| Ethyl alcohol | 7.50 | 7.50 |
| Polyoxyethylene (20) sorbitan monoisostearate | 0.20 | 0.45 |
| Acetic acid | — | 0.20 |
| Boric acid | 0.08 | 0.08 |
| Flavor | 0.04 | 0.17 |
| Coloring agent | 0.05 | 0.14 |
| Sweetening agent (saccharin) | 0.05 | 0.09 |
| Water | balance | balance |
| Adjust pH to | pH 2.70 | pH 3.95 |

Ten ml. portions of each of the above solutions were mixed and immediately (within ten seconds) placed in the mouth whereupon the 20 ml. mixture was held in contact with the teeth for from 15 to 30 seconds. The mixture had a pH of about 2.7. This procedure was repeated twice a day for three weeks. Observation indicated that remineralization of demineralized enamel had occurred. The remineralized enamel was more resistant to demineralization than was the original enamel.

What is claimed is:

1. A method for remineralizing demineralized tooth enamel, said method comprising the steps of
   (a) forming a metastable aqueous solution comprising calcium ions and phosphate ions in a molar ratio ranging from about 0.01 to about 100 and having a pH of from about 2.5 to about 4 by admixing
      (i) a solution containing calcium ions in an amount ranging from about 0.005% to about 5%, and containing calcium ions in an amount such and having a pH such as to obtain said metastable solution on admixture, and
      (ii) a solution containing phosphate ions in an amount ranging from 0.005% to about 5%, and containing phosphate ions in an amount such and having a pH such as to obtain said metastable solution on admixture, and
   (b) within 5 minutes after its formation and within the period of its temporary stability, applying said formed metastable aqueous solution to the tooth surface in the oral cavity in such an amount and for a time period ranging from about 10 seconds to about 3 minutes so that the pH of the solution rises to foster precipitation within the tooth to thereby effect remineralization at the demineralized tooth subsurface.

2. The method of claim 1 in which said metastable solution has a pH on the order of from about 2.7 to about 3.3.

3. The method of claim 2 in which said metastable solution is formed by admixing a solution containing from about 0.005% to about 5% calcium ions and from about 0.005% to about 5% indium ions with a solution containing from about 0.005% to about 5% phosphate ions.

4. The method of claim 2 in which said metastable solution is formed by admixing a solution containing from about 0.005% to about 5% calcium ions with a solution containing from about 0.005% to about 5% phosphate ions and from about 0.005% to about 5% fluoride ions.

5. The method of claim 2, in which said metastable solution is formed by admixing a solution containing from about 0.005% to about 5% calcium ions and from about 0.005% to about 5% indium ions with a solution containing from about 0.005% to about 5% phsophate ions and from about 0.005% to about 5% fluoride ions.

6. The method of claim 2 in which, in step (b), said metastable solution is applied within 1 minute after it is formed.

7. The method of claim 1 in which the metastable aqueous solution comprises calcium ions and phosphate ions in a molar ratio ranging from about 0.2 to about 5.

8. The method of claim 7 in which the metastable aqueous solution comprises calcium ions and phosphate ions in a molar ratio of about 1.67.

9. The method of claim 1 in which the amount of metastable aqueous solution placed in the mouth contains calcium ions and phosphate ions to provide at least 0.001 gram of calcium phosphate calculated as $Ca_3(PO_4)_2$.

10. The method of claim 9 in which the amount of metastable aqueous solution placed in the mouth contains calcium ions and phosphate ions to provide more than 0.1 gram of calcium phosphate calculated as $Ca_3(PO_4)_2$.

11. The method of claim 1 in which the metastable aqueous solution is in the form of a mouthwash.

12. The method of claim 1 in which the metastable aqueous solution is in the form of a toothpaste.

* * * * *

UNITED STATES PATENT OFFICE
CERTIFICATE OF CORRECTION

PATENT NO. : 4,080,440
DATED : March 21, 1978
INVENTOR(S) : David N. DiGiulio and Robert J. Grabenstetter It is certified that error appears in the above-identified patent and that said Letters Patent are hereby corrected as shown below:

Column 7, line 35, "Padar" should read --Pader--.

Column 8, line 33, "Toothpoaste" should read --toothpaste--.

Example I caption "Cationic Part 5 by Weight" should read --Cationic Part % by Weight--. (This error occurs twice.)

Example I ingredient "Silica zerogel abrasive (Syloid 63 from the Grace Davison Chem. Co.)" should read --Silica xerogel abrasive (Syloid 63 from the Grace Davison Chem. Co.)--.

Example I ingredient "Polyoxyethylene (200 sorbitan monoisostearate" should read --Polyoxyethylene (20) sorbitan monoisostearate--.

Signed and Sealed this

Eighteenth Day of July 1978

[SEAL]

Attest:

RUTH C. MASON
Attesting Officer

DONALD W. BANNER
Commissioner of Patents and Trademarks